US009689795B2

(12) United States Patent
Meyers et al.

(10) Patent No.: US 9,689,795 B2
(45) Date of Patent: Jun. 27, 2017

(54) METHODS AND SYSTEMS TO ANALYZE A GAS-MIXTURE

(71) Applicant: General Electric Company, Schenectady, NY (US)

(72) Inventors: Mark Marshall Meyers, Mechanicville, NY (US); David Peter Robinson, Lisburn (GB); Sandip Maity, Bangalore (IN); Nagapriya Kavoori Sethumadhavan, Bangalore (IN)

(73) Assignee: General Electric Company, Niskayuna, NY (US)

( * ) Notice: Subject to any disclaimer, the term of this patent is extended or adjusted under 35 U.S.C. 154(b) by 120 days.

(21) Appl. No.: 14/668,099

(22) Filed: Mar. 25, 2015

(65) Prior Publication Data
US 2016/0282260 A1  Sep. 29, 2016

(51) Int. Cl.
*G01J 3/02* (2006.01)
*G01N 21/25* (2006.01)
(Continued)

(52) U.S. Cl.
CPC ............ *G01N 21/255* (2013.01); *G01J 3/021* (2013.01); *G01J 3/42* (2013.01); *G01J 3/433* (2013.01);
(Continued)

(58) Field of Classification Search
CPC .......................... G01N 21/255; G01N 33/0009
See application file for complete search history.

(56) References Cited

U.S. PATENT DOCUMENTS 7,582,219 B1 *  9/2009  Asai ..................... G02B 26/101
                                                                216/24
7,800,751 B1    9/2010  Silver et al.
(Continued)

FOREIGN PATENT DOCUMENTS

CN       101644673 A    2/2010
EP         1070943 A1    1/2001
(Continued)

OTHER PUBLICATIONS

Xia et al., "Signal processing method of ambient trace-gas monitoring with tunable diode laser absorption spectroscopy", Information, Computing and Telecommunication, 2009. YC-ICT '09. IEEE Youth Conference on, IEEE Xplore, pp. 506-509, Sep. 20-21, 2009, Conference Location : Beijing.
(Continued)

*Primary Examiner* — Tony Ko
(74) *Attorney, Agent, or Firm* — Nitin N. Joshi

(57) ABSTRACT

A system is presented. The system includes an absorption cell filled-with a gas-mixture, a mirror-cum-window comprising a first portion that acts as a first mirror and a second portion that acts as a first window, a second mirror, a plurality of radiation sources to generate a plurality of light beams directed into the absorption cell through the first window followed by reflection of the plurality of light beams between the first mirror and the second mirror to irradiate the gas-mixture resulting in generation of a plurality of transmitted light beams passing out of the absorption cell through the second window, a detector that detects at least one characteristic of the plurality of transmitted light beams resulting in generation of one or more response signals, and a processing subsystem that analyzes the gas-mixture at least based on the one or more response signals.

16 Claims, 3 Drawing Sheets

(51) Int. Cl.
*G01N 33/00* (2006.01)
*G01J 3/433* (2006.01)
*G01N 21/03* (2006.01)
*G01J 3/42* (2006.01)
*G01N 21/3504* (2014.01)

(52) U.S. Cl.
CPC ....... *G01N 21/031* (2013.01); *G01N 33/0009* (2013.01); *G01N 21/3504* (2013.01)

(56) References Cited

U.S. PATENT DOCUMENTS

| | | | |
|---|---|---|---|
| 7,903,704 B2 | 3/2011 | Patel et al. | |
| 8,395,777 B2 | 3/2013 | Rao | |
| 8,953,926 B1 * | 2/2015 | Kelly | H05B 33/02 362/335 |
| 2011/0270113 A1 | 11/2011 | Heyne et al. | |
| 2013/0221224 A1 * | 8/2013 | Maksyutenko | G01N 21/0303 250/343 |
| 2014/0036954 A1 | 2/2014 | Maity et al. | |
| 2014/0049777 A1 | 2/2014 | Sun et al. | |
| 2014/0253922 A1 | 9/2014 | Liu et al. | |

FOREIGN PATENT DOCUMENTS

| | | |
|---|---|---|
| EP | 1167949 A1 | 1/2002 |
| WO | 2008079032 A2 | 7/2008 |
| WO | 2014029971 A1 | 2/2014 |

OTHER PUBLICATIONS

Capasso, F. et al., "High performance quantum cascade lasers for the $\lambda=4$ to 17 μm region and their chemical sensing applications", Indium Phosphide and Related Materials, 2000. Conference Proceedings. 2000 International Conference on, IEEE Xplore, pp. 262-265, 2000, Conference Location : Williamsburg, VA.

Tarsitano et al., "Multilaser Herriott Cell for Planetary Tunable Laser Spectrometers", Applied Optics, Volume No. 16, Issue No. 28, pp. 6923-6935, Oct. 1, 2007.

European Search Report and Opinion issued in connection with corresponding EP Application No. 16160980.5 on Sep. 5, 2016.

* cited by examiner

METHODS AND SYSTEMS TO ANALYZE A GAS-MIXTURE

BACKGROUND

The subject matter disclosed herein relates to dissolved gas analysis using spectroscopy. Specifically, the subject matter relates to accurate measurement of gas concentrations using wavelength modulation spectroscopy.

Electrical equipment such as transformers use fluids such as castor oil, mineral oil and synthetic oils for insulation purposes. The parameters of the fluid are indicative of incipient faults in the electrical equipment. The parameters of the fluid among other things include information of total combustible gas (TCG). Examples of total combustible gas include carbon monoxide, carbon dioxide, hydrocarbons, oxygen and nitrogen. Specifically, carbon monoxide and carbon dioxide increase in concentration with thermal aging and degradation of insulation of the electrical equipment. Furthermore, hydrocarbons such as acetylene and ethylene increase in concentration due to dielectric breakdown caused due to corona and arcing. Further, concentrations of oxygen and nitrogen are indicative of condition of a gas pressurizing system of the equipment. Therefore, technique of dissolved gas analysis (DGA) is employed to determine the concentration of the gas components in the fluid used in the electrical equipment to predict the incipient fault.

Methods of analyzing the gas concentrations from the fluid-samples extracted from the equipment employ spectroscopic techniques. Conventional spectroscopic techniques include off line DGA techniques and absorption spectroscopy based techniques. However, off line DGA techniques are affected by uncertainties issues. Furthermore, techniques employing direct absorption spectroscopic signals are less sensitive with poor signal-to-noise ratio. In general, conventional spectroscopic techniques determine the concentrations of the gas component in a limited range of concentrations and are based on modulating the light beam to improve the sensitivity of detection. Measurements from spectroscopic techniques such as wavelength modulation spectroscopy are affected by the ambient conditions of the gas, especially the ambient pressure conditions of the dissolved gas.

Furthermore, long path lengths may be needed to increase signal to noise ratio in absorption spectroscopy. This is achieved by using multi-pass cells (MPCs), where a laser beam bounces off between two mirrors in a cavity containing the gas mixture. However, typical MPCs may be complex, bulky and expensive due to usage of multiple optical elements and multiple lasers.

BRIEF DESCRIPTION

In accordance with one embodiment, a system is presented. The system includes an absorption cell filled-with a gas-mixture comprising a mirror-cum-window comprising a first portion that acts as a first mirror and a second portion that acts as a first window, a second mirror, a plurality of radiation sources to generate a plurality of light beams directed into the absorption cell through the first window followed by reflection of the plurality of light beams between the first mirror and the second mirror to irradiate the gas-mixture resulting in generation of a plurality of transmitted light beams passing out of the absorption cell through the second window, a detector that detects at least one characteristic of the plurality of transmitted light beams resulting in generation of one or more response signals, and a processing subsystem that analyzes the gas-mixture at least based on the one or more response signals.

In accordance with another embodiment, a system is presented. The system includes an absorption cell filled-with a gas-mixture, a first mirror-cum-window comprising a first portion that acts as a first mirror and a second portion that acts as a first window, a second minor-cum-window comprising a first portion that acts as a second mirror and a second portion that acts as a second window, a plurality of radiation sources to generate a plurality of light beams directed into the absorption cell through the first window followed by reflection of the plurality of light beams between the first mirror and the second mirror to irradiate the gas-mixture resulting in generation of a plurality of transmitted light beams, a detector that detects at least one characteristic of the plurality of transmitted light beams resulting in generation of one or more response signals, and a processing subsystem that analyzes the gas-mixture at least based on the one or more response signals.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

Unless defined otherwise, technical and scientific terms used herein have the same meaning as is commonly understood by one of ordinary skill in the art to which this disclosure belongs. The terms "a" and "an" do not denote a limitation of quantity, but rather denote the presence of at least one of the referenced items. The term "or" is meant to be inclusive and mean one, some, or all of the listed items. The use of "including," "comprising" or "having" and variations thereof herein are meant to encompass the items listed thereafter and equivalents thereof as well as additional items. The terms "control system" or "controller" may include either a single component or a plurality of components, which are either active and/or passive and are connected or otherwise coupled together to provide the described function or functions.

Figure 1:
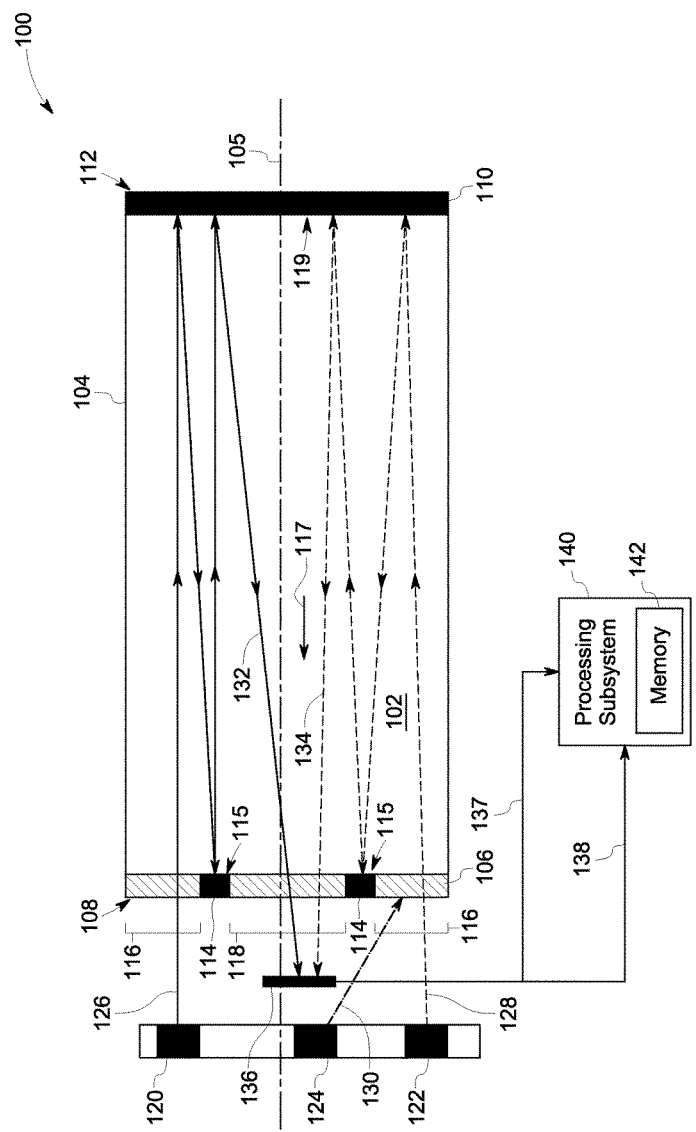
FIG. 1 is an example of a block diagram of a gas-analyzer system for analyzing a gas-mixture, in accordance with certain embodiments of the present techniques.

FIG. 1 is an example of a block diagram of a gas-analyzer system 100 for analyzing a gas-mixture 102, in accordance with certain embodiments of the present techniques. In the presently contemplated configuration, the system 100 is an electromagnetic radiation absorption spectroscopy device. The system 100 includes an absorption cell 104 that is filled with the gas-mixture 102. The absorption cell 104 for example may be a cylinder or a cuboid. In one embodiment, the absorption cell 104 may be exposed to the atmosphere when gases present in the atmosphere are required to be detected.

The system 100 includes a mirror-cum-window 106 located at a first end 108 of the absorption cell 104, and a second mirror 110 located at a second end 112 that is opposite to the first end 108 of the absorption cell 104. The mirror-cum-window 106 includes a first portion 114 that acts as a first mirror 114 and a second portion 116 that acts as a first window 116. The minor-cum-window 106 and the second mirror 110 are located on the opposite ends 108, 112 of the absorption cell 104 such that a reflective surface 115 of the first mirror 114 faces a reflective surface 119 of the second mirror 110.

In one embodiment, the minor-cum-window 106 is a circular plate or a square plate. In one embodiment, the second window 116 surrounds a periphery of the first mirror 114. The minor-cum-window 106 may be made of a material comprising wedged substrate, such as, Fused Silica, Excimer Grade Fused Silica, calcium fluoride, zinc selenide, magnesium fluoride, germanium, glass, sapphire, or the like. The material, for example, may be chosen based on a radiation wavelength range. The material of the substrate should be such that it transmits the incident laser radiation. The first mirror 114, for example is made by coating a patterned reflective material on a wedged substrate. The patterned reflective material, for example, may include gold, silver, aluminum, reflecting dielectrics, or the like. In one embodiment, the minor-cum-window 106 further comprises a third portion 118 that acts a second window 118. In one embodiment, when the absorption cell 104 is exposed to the environment, the first window 116 and/or the second window 118 is an aperture formed in the minor-cum-window 106. In one embodiment, when the mirror-cum-window 106 comprises the second window 118, then the first window 116 and/or the first mirror 114 are annular in shape, and the second window 118 may be circular in shape but not annular in shape and the first mirror 114 surrounds the periphery of the circular second window 118.

Figure 2A:
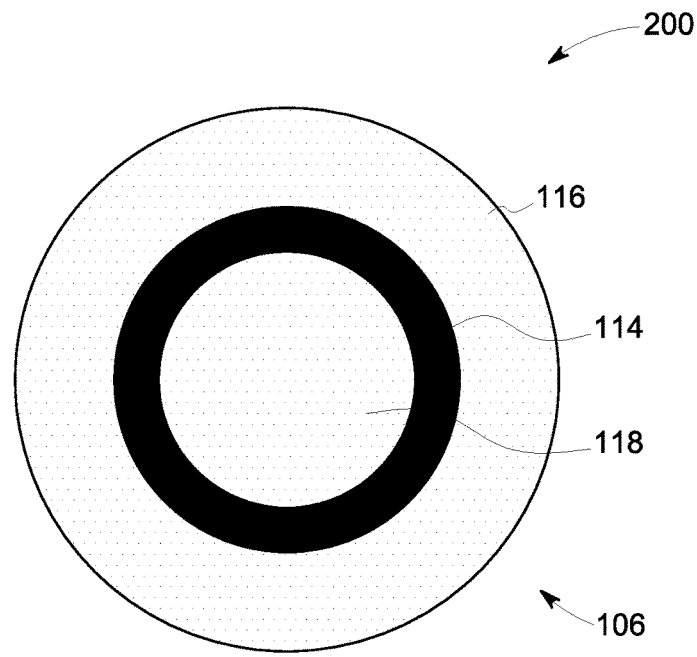
FIG. 2(A) shows a view of the mirror-cum-window when viewed in the direction of the arrow shown in FIG. 1, in accordance with one embodiment.

FIG. 2(A) shows a view 200 of the mirror-cum-window 106 when viewed in the direction of an arrow 117 shown in FIG. 1, in accordance with one embodiment. In the embodiment of FIG. 2(A), the mirror-cum-window 106 includes the first mirror 114, the first window 116 and the second window 118. While in the embodiment of FIG. 2(A), the mirror-cum-window 106, the first mirror 114, the first window 116 and the second window 118 are circular, however the mirror-cum-window 106, the first mirror 114, the first window 116 and the second window 118 may be of any other shape. As shown in FIG. 2(A), the first window 116 surrounds the periphery of the first mirror 114, and the first mirror 114 surrounds the periphery of the second window 118. Furthermore, in the embodiment of FIG. 2A, the first mirror 114 and the first window 116 are of annular shape, and the second window 118 is of circular shape but not annular shape.

Figure 2B:
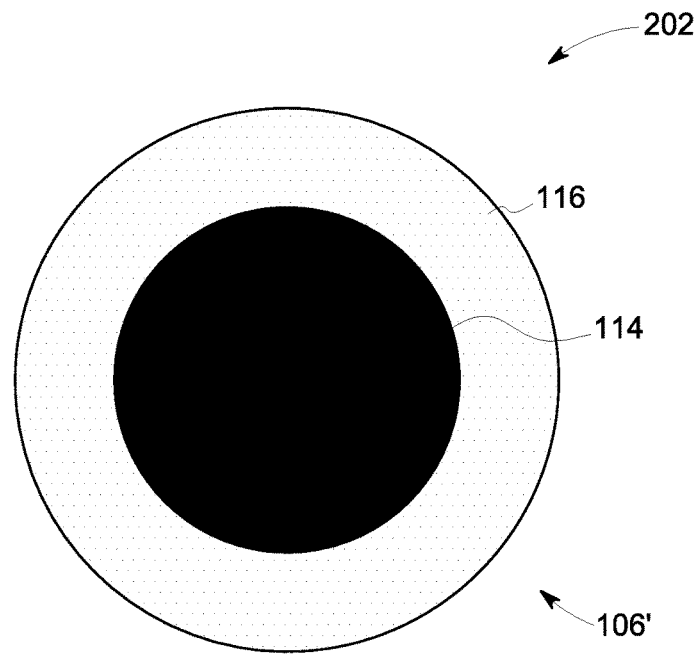
FIG. 2(B) shows a view of a mirror-cum-window when viewed in the direction of the arrow shown in FIG. 1, in accordance with another embodiment.

Referring back to FIG. 1, in certain embodiments, the mirror-cum-window 106 may not include the second window 118. In one embodiment, when the mirror-cum-window 106 does not comprise the second window 118, then the first mirror 114 is circular in shape but not annular shape. FIG. 2(B) shows a view 202 of a mirror-cum-window 106' when viewed in the direction of the arrow 117 shown in FIG. 1, in accordance with another embodiment. FIG. 2(B) shows an embodiment of the mirror-cum-window 106' that includes the first mirror 114 and the first window 116, and does not include the second window 118. As shown in FIG. 2(B), the first window 116 is annular in shape, the first mirror 114 is circular in shape but not annular in shape. Furthermore, the first window 116 surrounds the periphery of the first mirror 114.

Referring back to FIG. 1, due to the first mirror 114 and the first window 116, the single mirror-cum-window 106 acts as one or more windows and a mirror. In the presently contemplated configuration, the minor-cum-window 106 is capable of transmitting light into the absorption cell 104 through the first window 116 about the periphery of the first mirror 114, and reflecting light about the center or annular area of the first mirror 114. Furthermore, in the embodiment when the second window 118 is present in the minor-cum-window 106, the minor-cum-window 106 is further capable of transmitting light out through the second window 118 and about the center of the second window 118.

Furthermore, the system 100 includes a plurality of radiation sources 120, 122, 124. In the presently contemplated configuration, the radiation sources 120, 122, 124 are tunable radiation sources. While the presently contemplated configuration shows three radiation sources 120, 122, 124, however the system 100 may include more or less radiation sources. The radiation sources 120, 122, 124, for example, may be a coherent source, an incoherent source, a visible light source, an infrared source, or the like. The coherent source, for example, is a tunable laser source, a diode laser, a laser, a Quantum cascade laser, or the like. The incoherent source may be a Light Emitting Diode (LED). The radiation sources 120, 122, 124 may be radially located with respect to an axis 105 passing through a center of the minor-cum-window 106. The radiation sources 120, 122, 124, for example, may be located at about farthest possible distance from one another. Particularly, in one embodiment, the plurality of radiation sources 120, 122, 124 may be located at a substantially equal angular distance from one another. For example, in the presently contemplated configuration, the radiation sources 120, 122, 124 are circularly located at an angular distance of about 120 degrees from one another. In one embodiment, one or more of the radiation sources 120, 122, 124 are mounted in housings with adjustable temperature, current, collimation and pointing. In one embodiment, each of the radiation sources 120, 122, 124 is mounted in a separate housing with adjustable temperature, current, collimation and pointing. In one embodiment, each of the radiation sources 120, 122, 124 is located on a single imaginary plane. In another embodiment, one or more of the radiation sources 120, 122, 124 are on different imaginary planes. In the presently contemplated configuration, the plurality of radiation sources 120, 122, 124 are arranged in a circular fashion such that locations of the plurality of radiation sources 120, 122, 124 are non-collinear.

The radiation sources 120, 122, 124 generate and direct a plurality of light beams 126, 128, 130 into the absorption cell 104. In the presently contemplated configuration, the first radiation source 120 generates and directs the first light beam 126 into the absorption cell 104. Similarly, the second radiation source 122 generates and directs the second light beam 128 into the absorption cell 104. Additionally, the third radiation source 124 generates and directs the third light beam 130 into the absorption cell 104. It is noted that due to space constraints and two dimensional view of the system 100, the third light beam 130 is not shown inside the absorption cell 104 and is shown via a dotted line. In one embodiment, at a time stamp t the radiation sources 120, 122, 124 simultaneously generate the light beams 126, 128, 130 characterized by different absorption wavelengths and different modulation frequencies with respect to one another.

The direction of the light-beams 126, 128, 130 into the absorption cell 104 irradiates the gas-mixture 102 filled in the absorption cell 104. In the presently contemplated configuration the absorption cell 104 is a multi-pass absorption cell 104 and hence the light beams 126, 128, 130 are reflected multiple times between the first mirror 114 and the second mirror 110 to increase a total optical path length of the light beams 126, 128, 130 in a constant length of the absorption cell 104 to increase detection sensitivity and analysis sensitivity of the gas-analyzer system 100. The irradiation of the gas-mixture 102 by the light-beams 126, 128, 130 results in absorption of the photons of the light-beams 126, 128, 130 by the gas-mixture 102. For example, when the first light beam 126 is characterized by an absorption wavelength W1 of a first individual gas $G_1$ present in the gas-mixture 102, then the first individual gas G1 present in the gas-mixture 102 absorbs at least some photons of the first light beam 126. Similarly, when the second light beam 128 is characterized by an absorption wavelength W2 of a second individual gas $G_2$ present in the gas-mixture 102, then the second individual gas G2 absorbs at least some photons of the second light beam 128. Similarly, when the third light beam 130 is characterized by an absorption wavelength W3 of a third individual gas G3 present in the gas-mixture 102, then the third individual gas G3 absorbs at least some photons of the third light beam 130.

The absorption of the photons of the light beams 126, 128, 130 by the gas-mixture 102 changes one or more characteristic of the light beams 126, 128, 130. Hereinafter, the changed light beams 126, 128, 130 are referred to as "transmitted light beams". In the presently contemplated configuration, the absorption of the photons of the first light beam 126 changes at least one characteristic of the first light beam 126 to generate a first transmitted light beam 132. Similarly, in the presently contemplated configuration, the absorption of the photons of the second light beam 128 by the gas-mixture 102 changes at least one characteristic of the second light beam 128 to generate a second transmitted light beam 134. Furthermore, absorption of the third light beam 130 changes at least one characteristic of the third light beam 130 to generate a third transmitted light beam (not shown in FIG. 1 due to space constraint).

The system 100 further includes a detector 136 operationally coupled to the absorption cell 104. The position of the detector 136 is based on the presence or absence of the second window 118 in the mirror-cum-window 106. Since in the presently contemplated configuration, the mirror-cum-window 106 includes the second window 118, therefore the detector 136 and the second window 114 are located on the same end 108 of the absorption cell 104, and the detector 136 is parallel to the mirror-cum-window 106. Another embodiment of the system 100 wherein the mirror-cum-window 106 does not include the second window 118 which leads to another position of the detector 136 are shown with reference to FIG. 3.

The detector 136 receives the first transmitted light beam 132, the second transmitted light beam 134 and the third transmitted light beam (not shown). Furthermore, the detector 136 generates one or more response signals based on at least one characteristic of the transmitted light beams 132, 134. The characteristic of the transmitted light beams 132, 134, for example may include an intensity and/or energy of the transmitted light beams 132, 134. In the presently contemplated configuration, the detector 136 determines a first response signal 137 based on a characteristic of the first transmitted light beam 132. Furthermore, in the presently contemplated configuration, the detector 136 determines a second response signal 138 based on a characteristic of the second transmitted light beam 134. Similarly, the detector 136 may determine a third response signal (not shown) based on a characteristic of the third transmitted light beam (not shown). It is noted that while in the presently contemplated configuration three response signals 137, 138 are generated, more or less than three response signals may be generated based on the number of radiation sources used in the system 100. The response signals 137, 138, for example, are representative of intensity of the transmitted light beams 132, 134 as a function of wavelength.

Furthermore, the system 100 includes a processing subsystem 140 in operational communication with the detector 136. The processing subsystem 140 includes at least one arithmetic logic unit, a microprocessor, a general purpose controller or a processor array to perform the desired computations or run the computer program. The processing subsystem 140 includes a memory 142. The memory 142 may be a non-transitory storage medium. For example, the memory 142 may be a dynamic random access memory (DRAM) device, a static random access memory (SRAM) device, flash memory or other memory devices. In one embodiment, the memory 142 may include a non-volatile memory or similar permanent storage device, media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices.

The processing subsystem 140 receives the response signals 137, 138. In the presently contemplated configuration, the processing subsystem 140 is programmed to analyze the gas-mixture 102 at least based on the response signals 137, 138. For example, the processing subsystem 140 may apply Beer Lambert law to measure concentrations of individual gases present in the gas-mixture 102 based on an amount of absorption of the light beams 126, 128, 130 at a determined wavelength by the gas-mixture 102. The amount of absorption of the light beams 126, 128, 130, for example, may be determined based on the intensity of the light-beams 126, 128, 130 and the response signals 137, 138.

In the presently contemplated configuration, the processing subsystem 140 may determine a presence and concentration of the individual gas G1 in the gas-mixture 102 based on an amount of absorption of the light beam 126 by the gas-mixture 102, wherein the amount of absorption of the light beam 126 may be determined based on the response signal 137 and an intensity of the light beam 126. Similarly, in the presently contemplated configuration, the processing subsystem 140 may determine a presence and concentration of the individual gas G2 in the gas-mixture 102 based on an amount of absorption of the light beam 128 by the gas-mixture 102, wherein the amount of absorption of the light beam 128 may be determined based on the response signal 138 and an intensity of the light beam. 128 in the gas-mixture 102. Similarly, the processing subsystem 140 may determine a presence and concentration of the individual gas G2 at least based on the characteristic of the second response signal 138.

Figure 3:
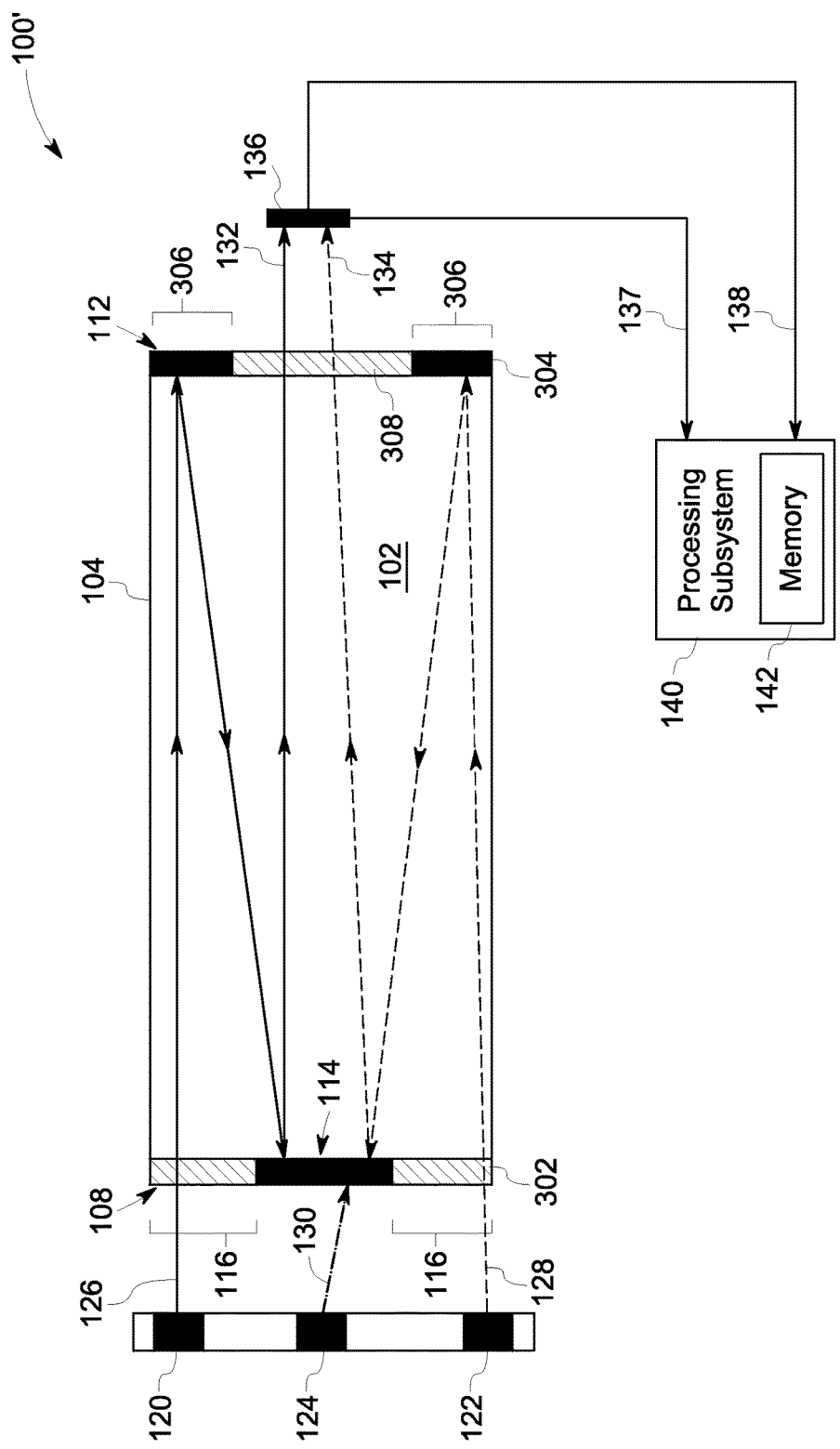
FIG. 3 is a block diagram of a gas-analyzer system for analyzing the gas-mixture, in accordance with certain embodiments of the present systems.

Referring now to FIG. 3, a block diagram of a gas-analyzer system 100' for analyzing the gas-mixture 102, in accordance with certain embodiments of the present systems is presented. Particularly, the gas-analyzer system 100' is an embodiment of the system 100 presented in FIG. 1. In the presently contemplated configuration, the system 100' includes a first mirror-cum-window 302 and a second mirror-cum-window 304. The first mirror-cum-window 302 is located on the first end 108 of the absorption cell 104 and the second mirror-cum-window 304 is located on the opposite end 112 of the absorption cell 104. In the presently contemplated configuration, the first mirror-cum-window 302 is similar to the mirror-cum-window 106' shown with reference to FIG. 2B that includes the first window 116 surrounding the periphery of the first mirror 114 and does not include the second window 118. Furthermore, the second mirror-cum-window 304 includes a first portion 306 that acts as a second mirror 306, and a second portion 308 that acts as a second window 308. In the presently contemplated configuration, the first window 116 surrounds the periphery of the first mirror 114 of the first mirror-cum-window 106, and the second mirror 306 surrounds a periphery of the second window 308. The second mirror 306 surrounds a periphery of the second window 308. In the presently contemplated configuration, the second mirror 306 is annular in shape that surrounds the circular and non-annular second window 308. As shown in FIG. 3, the first mirror-cum-window 302 and the radiation sources 120, 122, 124 are located around the first end 108 of the absorption cell 104, and the second mirror-cum-window 304 and the detector 136 is located around the second end 112 of the absorption cell 104.

Similar to FIG. 1, the radiation sources 120, 122, 124 generate and direct the light beams 126, 128, 130, respectively into the absorption cell 104 to irradiate the gas-mixture 102 resulting in generation of the transmitted light beam 132, 134. The detector 136 receives the transmitted light beams 132, 134 from the absorption cell 104 and generates the response signals 137, 138 based on the at least one characteristic of the transmitted light beams 132, 134. Furthermore, as discussed with reference to FIG. 1, the processing subsystem 140 receives the response signals 137, 138 from the detector 136, and analyzes the gas-mixture 102 at least based on the response signals 136, 138. For example, the processing subsystem 140 may analyze the gas-mixture 102 using a Beer Lambert law.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system, comprising:
   an absorption cell filled-with a gas-mixture, comprising:
     a mirror-cum-window comprising a first portion that acts as a first mirror, a second portion that acts as a first window, and a third portion that acts as a second window;
     a second mirror;
   a plurality of radiation sources to generate a plurality of light beams directed into the absorption cell through the first window followed by reflection of the plurality of light beams between the first mirror and the second mirror to irradiate the gas-mixture resulting in generation of a plurality of transmitted light beams passing out of the absorption cell through the second window;
   a detector that detects at least one characteristic of the plurality of transmitted light beams resulting in generation of one or more response signals; and
   a processing subsystem that analyzes the gas-mixture at least based on the one or more response signals,
   wherein the mirror-cum-window and the detector are located about a first end of the absorption cell, and wherein a reflective surface of the first mirror located around the first end of the absorption cell faces a reflective surface of the second mirror located around a second end of the absorption cell.

2. The system of claim 1, wherein the first window surrounds a periphery of the first mirror.

3. The system of claim 1, wherein the first mirror is made by coating a patterned reflective material on a wedged surface, and wherein the patterned reflective material comprises gold, silver, aluminum, reflecting dielectrics, or combinations thereof.

4. The system of claim 1, wherein the first window is characterized by an annular shape and the first mirror is characterized by a circular shape.

5. The system of claim 1, wherein the first mirror surrounds a periphery of the second window.

6. The system of claim 5, wherein the first mirror and the first window are characterized by an annular shape and the second window is characterized by a circular shape.

7. The system of claim 1, wherein the first window and the second window are an aperture formed in the mirror-cum-window.

8. The system of claim 1, wherein the mirror-cum-window and the second mirror comprises at least one of a wedge shape, a flat shape, and a concave shape.

9. The system of claim 1, wherein the plurality of radiation sources are radially located with respect to an axis passing through a center of the mirror-cum-window.

10. The system of claim 1, wherein the plurality of radiation sources are located about the first end of the absorption cell.

11. The system of claim 1, wherein the plurality of radiation sources are arranged in a circular fashion such that locations of the plurality of radiation sources are non-collinear.

12. The system of claim 1, wherein the plurality of radiation sources are located on a single imaginary plane, or the plurality of radiation sources are located on different imaginary planes.

13. The system of claim 1, wherein the plurality of radiation sources are located at a substantially equal angular distance from one another.

14. A system, comprising:
   an absorption cell filled-with a gas-mixture, comprising:
     a first mirror-cum-window comprising a first portion that acts as a first mirror and a second portion that acts as a first window;
     a second mirror-cum-window comprising a first portion that acts as a second mirror and a second portion that acts as a second window;
   a plurality of radiation sources to generate a plurality of light beams directed into the absorption cell through the first window followed by reflection of the plurality of light beams between the first mirror and the second mirror to irradiate the gas-mixture resulting in generation of a plurality of transmitted light beams;
   a detector that detects at least one characteristic of the plurality of transmitted light beams resulting in generation of one or more response signals; and
   a processing subsystem that analyzes the gas-mixture at least based on the one or more response signals,
   wherein the first mirror-cum-window and the plurality of radiation sources are located around a first end of the absorption cell, and the second mirror-cum-window and the detector are located around a second end of the absorption cell, and wherein the second end is opposite to the first end of the absorption cell.

15. The system of claim 14, wherein the first window surrounds a periphery of the first mirror in the first mirror-cum-window, and the second mirror surrounds a periphery of the second window of the second mirror-cum-window.

16. A system, comprising:
- an absorption cell filled-with a gas-mixture, comprising:
  - a mirror-cum-window comprising a first portion that acts as a first mirror, a second portion that acts as a first window, and a third portion that acts as a second window;
  - a second mirror;
- a plurality of radiation sources to generate a plurality of light beams directed into the absorption cell through the first window followed by reflection of the plurality of light beams between the first mirror and the second mirror to irradiate the gas-mixture resulting in generation of a plurality of transmitted light beams passing out of the absorption cell through the second window;
- a detector that detects at least one characteristic of the plurality of transmitted light beams resulting in generation of one or more response signals; and
- a processing subsystem that analyzes the gas-mixture at least based on the one or more response signals,
- wherein the plurality of radiation sources and the mirror-cum-window are located about a first end of the absorption cell and the detector is located about a second end of the absorption cell, and wherein the second end of the absorption cell is opposite to the first end of the absorption cell.

* * * * *